United States Patent [19]

Tanaka

[11] Patent Number: 4,995,108
[45] Date of Patent: Feb. 19, 1991

[54] MARK-BEARING SUPPORT FOR DENTAL X-RAY FILM PACK

[75] Inventor: Hiroyuki Tanaka, Yokohama, Japan

[73] Assignee: Nix Company, Ltd., Tokyo, Japan

[21] Appl. No.: 389,303

[22] Filed: Aug. 3, 1989

[30] Foreign Application Priority Data

Dec. 19, 1988 [JP]  Japan ............................ 63-163540[U]

[51] Int. Cl.⁵ ................................................ A61B 6/14
[52] U.S. Cl. ...................................... 378/168; 378/169
[58] Field of Search ................................ 378/162–165, 378/168, 169

[56] References Cited

U.S. PATENT DOCUMENTS

| | | | |
|---|---|---|---|
| 1,564,269 | 12/1925 | Peyser | 378/162 |
| 1,917,433 | 7/1933 | Cressler | 378/162 |
| 2,390,397 | 12/1945 | Stadler | 250/57 |
| 2,426,286 | 8/1947 | Stadler | 378/165 |
| 2,733,354 | 1/1956 | Vloch | 250/67 |
| 4,075,494 | 2/1978 | Jermyn | 378/170 |
| 4,181,859 | 1/1980 | Vitalini | 378/164 |
| 4,194,122 | 3/1980 | Mitchell et al. | 378/165 |
| 4,274,006 | 6/1981 | Caine | 250/476 |
| 4,506,676 | 3/1985 | Duska | 378/162 |
| 4,633,493 | 12/1986 | Lindén | 378/168 |
| 4,764,948 | 8/1988 | Hurwitz | 378/162 |
| 4,860,331 | 8/1989 | Williams et al. | 378/163 |

FOREIGN PATENT DOCUMENTS 1258018  7/1968  Fed. Rep. of Germany .
2547014  5/1976  Fed. Rep. of Germany .

Primary Examiner—Carolyn E. Fields
Assistant Examiner—David P. Porta
Attorney, Agent, or Firm—Wegner, Cantor, Mueller & Player

[57]  ABSTRACT

A mark-bearing support for a dental X-ray film pack is disclosed. The support has an X-ray pervious bite portion to be clenched between upper and lower teeth and a support portion for temporarily holding the dental X-ray film pack thereon. The support portion is provided with a mark formed of an X-ray impervious material such as a lead-containing ink.

16 Claims, 3 Drawing Sheets

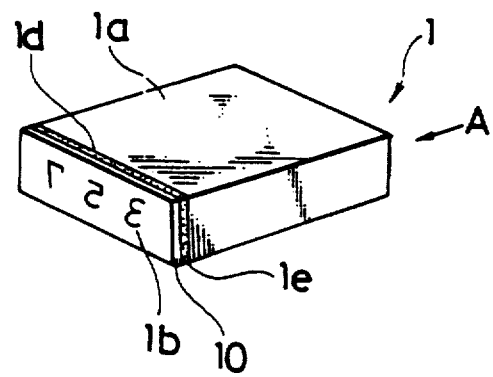
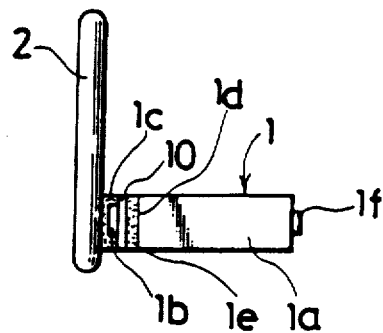
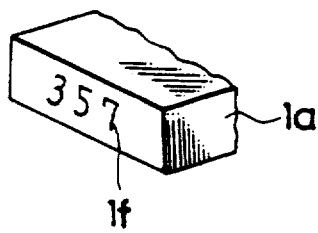
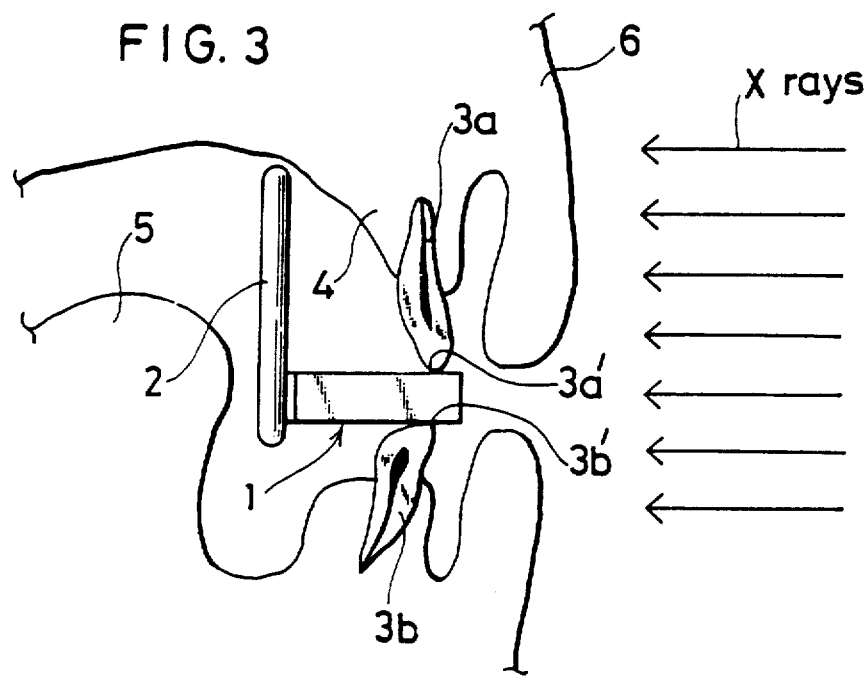

MARK-BEARING SUPPORT FOR DENTAL X-RAY FILM PACK

BACKGROUND OF THE INVENTION

1. Field of the Invention

This invention relates to a mark-bearing support for a dental X-ray-film pack containing a dental X-ray film therein. Upon taking an X-ray picture of a tooth, the mark-bearing support is used to temporarily hold the dental X-ray film pack thereon and to imprint the mark automatically on the dental X-ray film.

2. Description of the Related Art

In recent years, X-ray photographs of teeth have become an essential contribution toward more correct dental diagnosis and treatment. The procedure for obtaining such an X-ray photograph is to support along one side of the tooth in question, a dental X-ray film pack with an X-ray film enclosed in an envelope made of a material transparent to X-rays but opaque to light, then irradiating X-rays from the opposite side of the tooth. Support of such a dental X-ray film pack is effected by mounting the film pack on a support with adhesive, then clenching the support between upper and lower teeth. After exposure, the dental X-ray film pack is opened in a light-proof situation and the film is removed. It is then developed to obtain an X-ray picture of the tooth.

It is essential that each exposed X-ray film relates correctly to its corresponding patient. For this purpose, it was previously the practice to place the exposed X-ray film in an envelope and to write the name of the patient and the place and date of the photography on the envelope. However, this method is time consuming. Moreover, if the X-ray film and envelope should become separated for some reason, it can be extremely difficult to identify the patient of the X-ray film.

To overcome such a drawback, mark-bearing sheets on which some identification (numbers, alphabetical letters, symbols, or the like), printed in advance with an X-ray impervious material, have been used. Upon taking an X-ray photograph, a mark-bearing sheet is applied to a corner of a dental X-ray film pack. Instead of using such a mark-bearing sheet, a mark-applying apparatus has also been used to imprint a desired mark on an exposed X-ray film before its development. The use of such a mark-bearing sheet or mark-applying apparatus however requires not only the mark-bearing sheet or mark-applying apparatus additionally but also the yet further step of applying the mark-bearing sheet or setting the dental X-ray film pack on the mark-applying apparatus and then operating the mark-applying apparatus.

SUMMARY OF THE INVENTION

An object of this invention is to solve the problems of the conventional art, and to provide a mark-bearing support for a dental X-ray film pack, which requires neither the additional provision of any mark-bearing sheet or mark-applying apparatus nor any additional step for the application of a mark.

In one aspect of this invention, there is thus provided a mark-bearing support for a dental X-ray film pack. The support has an X-ray pervious bite portion to be clenched between upper and lower teeth and a support portion for temporarily holding the dental X-ray film pack thereon. The support portion is provided with a first mark formed of an X-ray impervious material.

In another aspect of this invention, there is also provided a process for the production of a plurality of similar mark-bearing supports. The process comprises:

printing a like number of first marks at predetermined intervals with an X-ray impervious ink on an X-ray pervious base sheet;

securing the base sheet on one side of an X-ray pervious base material;

applying a release sheet, one side of which bears an adhesive layer coated thereon, to the base sheet with the adhesive layer interposed between the release sheet and base sheet;

cutting the base material and base sheet between the individual first marks.

In a further aspect of this invention, there is also provided a process for the production of a plurality of similar mark-bearing supports. The process comprises:

printing a like number of marks at predetermined intervals with an X-ray impervious ink on one side of an X-ray previous base material;

applying a release sheet, one side of which bears an adhesive layer coated thereon, to the base material with the adhesive layer interposed between the release sheet and base material; and cutting the base material between the individual marks.

The dental X-ray film pack is supported on the mark-bearing support. The support with the film pack thereon is inserted into the mouth of a patient and clenched between the upper and lower teeth, thus holding the film pack at a desired position. The film pack is then exposed to X-rays through the upper or lower tooth, so that the mark is automatically imprinted on the X-ray film. Making the X-ray film correspond to the patient can therefore be extremely easy.

Since the mark formed of the X-ray impervious material is provided on the support for the dental X-ray film pack, it requires neither the additional provision of any conventional mark-bearing sheet or mark-applying apparatus nor any additional step for the application of a mark. Further, a dentist or X-ray technician is not troubled by the appropriate positioning of a mark on an X-ray film.

BRIEF DESCRIPTION OF THE DRAWINGS

The above and other objects, features and advantages of the present invention will become apparent from the following description and the appended claims, taken in conjunction with the accompanying drawings in which:

FIG. 1(*a*) is a perspective view of a support according to a first embodiment of this invention, in which a top release sheet and an underlying adhesive layer are omitted;

FIG. 1(*b*) is a fragmentary perspective view of the support of FIG. 1(*a*) as viewed in the direction of arrow A in FIG. 1(*a*);

FIG. 2 is a side view of the support of FIG. 1 with a dental X-ray film pack held thereon;

FIG. 3 is a fragmentary cross-sectional view of a mouth upon taking an X-ray photograph of teeth;

DETAILED DESCRIPTION OF THE INVENTION AND PREFERRED EMBODIMENT

Figure 4:
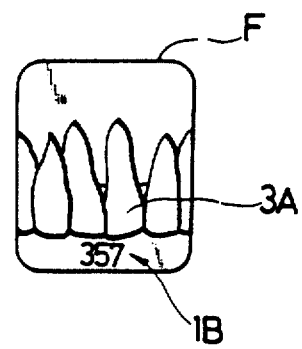
FIG. 4 is a plan view of the X-ray photograph.

Referring now to FIGS. 1(a), 1(b) and 2, the construction of the support according to the first embodiment of this invention will be described. The support is generally designated at numeral 1. The material of the support 1 is chosen from those having absolutely no toxicity because it is to be inserted into the mouth, a certain degree of softness because it is to be clenched between upper and lower teeth, and be X-ray pervious. Foamed polyethylene is an example of such a material. The support 1 is in the form of a block, more specifically a rectangular parallelepiped, and has a bite portion 1a to be clenched between the upper and lower teeth, a sheet 10 bearing a mark 1b printed thereon with a lead-containing ink, a first adhesive layer 1e fixedly holding the sheet 10 on an end surface 1d of the bite portion 1a, said end surface serving as a support portion, a second adhesive layer 1c coated over the mark 1b, and a second release sheet 7 provided over the second adhesive layer 1c (see FIG. 6).

An application method of the support 1 will next be described with reference to FIGS. 2, 3 and 4. FIG. 2 is a side view of the support 1, in which like portions as in FIGS. 1(a) and 1(b) are identified by like reference symbols. Numeral 2 indicates a dental X-ray film pack, in which an X-ray film is enclosed. Upon application, the release sheet 7 (see FIG. 6) is first peeled off to expose the second adhesive layer 1c. An end portion of the dental X-ray film pack 2 is then adhered to the second adhesive layer 1c of the support 1 as depicted in FIG. 2, so that the dental X-ray film pack 2 is temporarily held on the support 1. The support 1 with the dental X-ray film pack 2 adhered thereon is thereafter inserted into the mouth, whereby the dental X-ray film pack 2 is held at a desired position within the mouth.

FIG. 3 is a cross-sectional view illustrating how the dental X-ray film pack 2 is held within the mouth by the support 1. In FIG. 3, like portions as in FIG. 2 are identified by like reference symbols. Designated at symbol 3a is a tooth to be X-rayed. Symbol 3b indicates a tooth opposite to the tooth 3a. Symbols 3a',3b' designate the occlusal surfaces of the teeth 3a,3b, respectively. There are also shown a gum 4, a tongue 5 and a cheek 6.

Now, the support 1 with the dental X-ray film pack 2 adhered thereon is inserted into the mouth as shown in FIG. 2, and the support 1 is clenched at the bite portion 1a between the occlusal surfaces 3a',3b' of the teeth 3a,3b. As a result, the dental X-ray film pack 2 is supported upright along a rear wall of the tooth 3a as the object for X-ray photography. When X rays are then externally irradiated as indicated by arrows in FIG. 3, an X-ray image of the tooth 3a is projected onto the X-ray film contained inside the dental X-ray film pack 2. At the same time, X rays are also allowed to transmit through the support 1. Because of the mark 1b printed in reverse on the support 1 with the lead-containing ink, its reversed X-ray image is projected onto the X-ray film. After completion of X-ray photography in the above manner, the dental X-ray film pack 2 is removed from the mouth, then peeled off from the support 1. The pack 2 is thereafter opened in a light-proof situation such as a darkroom or darkbox so that the exposed X-ray film is taken out of the pack 2. The exposed X-ray film is then developed to obtain an X-ray photograph.

FIG. 4 is a plan view of the X-ray photograph obtained as described above. In the drawing, letter F indicates the X-ray photograph while symbol 3A designates the X-ray picture of the tooth 3a. It is noted that X-ray pictures of teeth adjacent to the tooth 3a have also been taken. Symbol 1B indicates an X-ray picture of the mark 1b. In the illustrated embodiment, the mark is "357".

Figure 5:
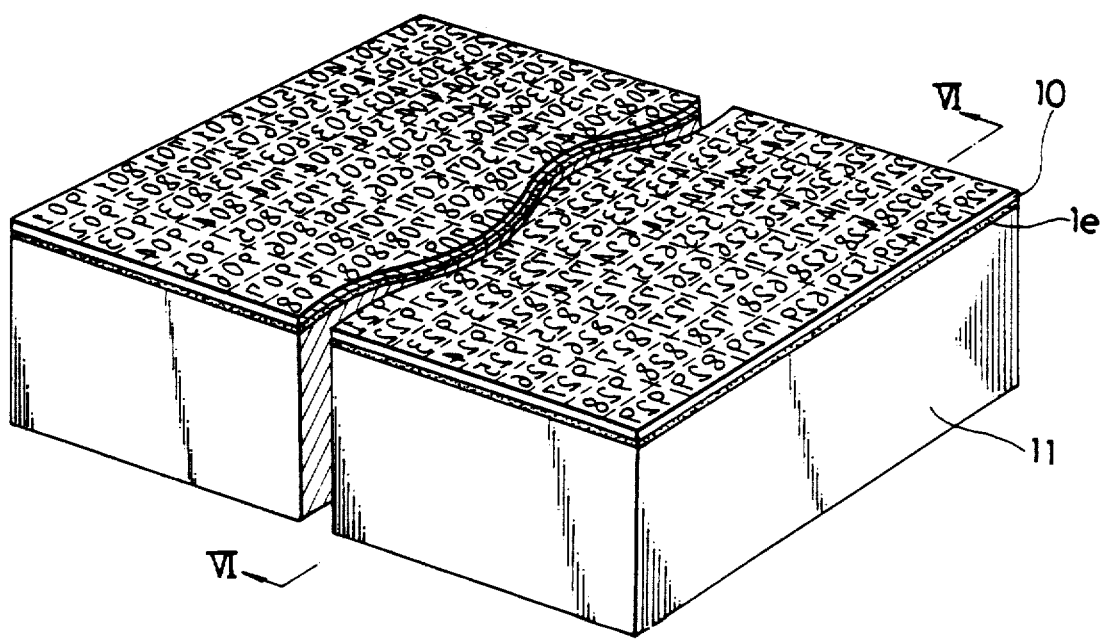
FIG. 5 is a perspective view illustrating a production process of a plurality of supports similar to the support of FIG. 1, in which a top release sheet and an underlying adhesive layer are omitted to show marks.
Figure 6:
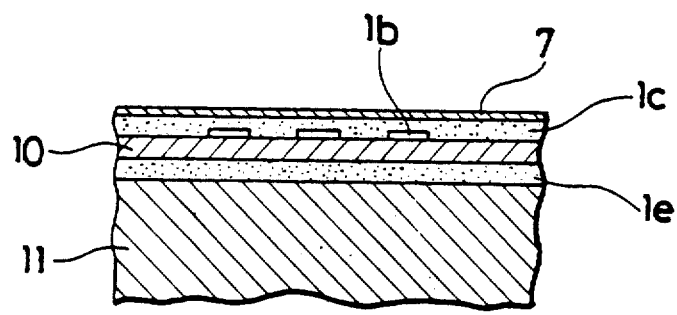
FIG. 6 is an enlarged fragmentary cross-sectional view taken in the direction of arrows VI,VI of FIG. 5, in which both the top release sheet and the underlying adhesive layer are shown.

Referring next to FIGS. 5 and 6, the production process of the support of FIG. 1 will be described. In FIG. 5, a top release sheet and an underlying second adhesive layer are omitted to shown marks as in FIG. 1. First of all, a plurality of marks 1b consisting individually of three digits are printed at predetermined intervals on one side of an X-ray pervious base sheet 10 which is made of paper by way of example. A base material 11 formed of a block-shaped polyethylene foam is next provided. After coating one side of the base material 11 with an adhesive and hence forming a first adhesive layer 1e, the base sheet 10 is affixed onto the first adhesive layer 1e with the marks facing outside. A release sheet 7 with an adhesive coated as a second adhesive layer 1c on one side thereof is then applied over the marks 1b in such a way that the second adhesive layer 1c is interposed between the release sheet 7 and the base sheet 10, whereby the structure shown in FIG. 5 is obtained. Although not seen in FIG. 5, marks 1f (see FIG. 2) of the same 3-digit figures are printed thereon with an X-ray pervious ink at the same intervals as the marks 1b on the opposite side of the base material 11 in such a way that the marks 1f are visible from the outside and are registered in position with the corresponding marks 1b printed with the lead-containing ink. The thus-formed structure is finally cut between the marks 1b, so that 240 mark-bearing supports similar to the support 1 are formed.

From the practical viewpoint, it is desirable to cut the base material 10 from the rear side, namely, from the side of the mark 1f between the marks 1f and also between the marks 1b as shown by dashed lines in FIG. 5 up to the first adhesive layer 1e so that the release sheet 7 is allowed to remain uncut. This is very convenient because the individual supports 1 are not separated and jumbled up but are kept in order. Upon application, the individual supports 1 are separated one after one in order from the release sheet 7. A dental X-ray film pack 2 is then applied to the second adhesive layer 1c of each support 1, so that the dental X-ray film pack 2 is temporarily held on the support 1.

Needless to say, it is necessary to choose the materials of the first adhesive layer 1e, second adhesive layer 1c and release sheet 7 so that each support 1 can be easily separated as an integral unit from the release sheet 7.

Figure 7:
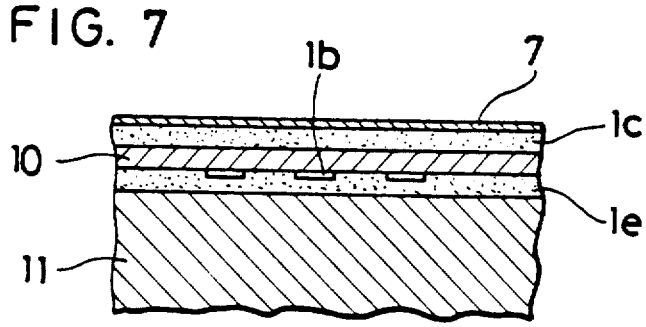
FIG. 7 is an enlarged fragmentary cross-sectional view of a modification of the support of FIG. 1, in which X-ray impervious marks are provided on an inner surface of an X-ray pervious base sheet, said surface facing a base material.

The modification of the support 1 of FIG. 1 is shown in FIG. 7. The marks 1b are printed with a lead-containing ink directly on the inner surface of the X-ray pervious base sheet 10. The marks 1b therefore remain inside the base sheet 10.

Figure 8:
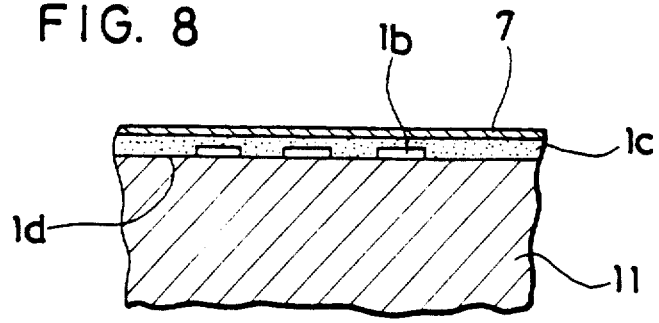
FIG. 8 is an enlarged fragmentary cross-sectional view illustrating a production process of a support according to a second embodiment of this invention, in which a surface release sheet and an underlying adhesive layer are omitted to show marks.

The production process of the supports according to the second embodiment of this invention will next be described with reference to FIG. 8. Similarly to the production process of the support according to the first embodiment, a base material 11 made of a block-shaped polyethylene foam is provided. Different marks 1b consisting respectively of 3-digit numbers are printed in reverse at predetermined intervals directly on one side of the base material 11 with a lead-containing ink. The same marks are printed on the opposite side of the base material 11 with an X-ray pervious ink in such a way that they are registered in position with the corresponding marks 1b printed with the lead-containing ink. An adhesive layer 1c is thereafter applied over the entire surface of said one side bearing the marks 1b and a release sheet 7 is applied onto the adhesive layer 1c. The resultant structure is then cut between the marks 1b.

FIG. 3 shows the position of the X-ray film pack for taking an X-ray picture of the upper tooth 3a. To X-ray the lower tooth 3b, it is only necessary to suspend the X-ray film pack 2 from the second adhesive layer 1c.

In each of the above embodiments, a 3-digit number is applied as a mark. The mark is however not necessarily limited to such a combination of numbers. It may consist of at least one of numbers and alphabetical letters.

A polyethylene foam is used to form the support in the above embodiments. The support can however be made of other materials so long as the above-described requirements are met.

A lead-containing ink is used as an illustrative X-ray impervious ink in the above embodiments. Other X-ray impervious inks can also be used, including those containing an X-ray impervious or absorptive material such as gold, silver, tungsten or barium.

The supports according to the first and second embodiments of this invention are in the form of a rectangular parallelepiped. Their shapes are however not necessarily limited to the rectangular parallelepiped.

The X-ray pervious bite portion can be formed of a plate of an X-ray pervious material, said plate having a thickness much smaller than the X-ray previous bite portion 1a, and the support portion may be formed of a similar plate which is formed integrally with the first-mentioned plate and extends at a right angle to the first-mentioned plate. This modified support therefore has an L- or T-like longitudinal cross-sectional shape.

As a further modification of the supports, the x-ray pervious bite portion may take a form similar to the X-ray pervious bite portion 1a except that the inside is hollow rather than solid. The X-ray pervious bite portion therefore has a rectangular frame-like shape when seen in a longitudinal cross-section.

In a still further modification, the X-ray pervious bite portion may be formed by bending a resilient X-ray pervious plate-like material over to have a somewhat flattened U-like shape when seen in a longitudinal cross-section. The support portion may then be formed of a similar plate in such a way that the support portion is formed integrally with the first-mentioned plate and extends at a right angle to the first-mentioned plate.

In a still further modification, the support may be formed of a first X-ray pervious plate member having an L- or T-like longitudinal cross-sectional shape and a second X-ray pervious plate member having a somewhat flattened U-like cross-section as viewed in the direction of the length of the support. A mark is applied with an X-ray impervious material or an outer surface of a shorter plate portion of the first X-ray pervious plate member and an adhesive layer is applied over the mark. The second X-ray pervious plate member is affixed to the first X-ray pervious plate member by means of the adhesive layer. The second X-ray pervious plate member therefore forms a pocket in which a dental X-ray film pack is fitted. It is preferable to impart resiliency to the second X-ray pervious plate member, because this resiliency can facilitate and ensure the holding of a dental X-ray film pack on the second X-ray pervious plate member, namely, on the support.

I claim:

1. A mark-bearing support for a dental X-ray film pack, said mark-bearing support comprising:
    an X-ray pervious bite portion adapted to be clenched between upper and lower teeth; and
    a support portion means for temporarily holding the dental X-ray film pack thereon;
    wherein the support portion is provided with a first mark formed of an X-ray impervious material; and
    wherein an X-ray pervious sheet bearing the first mark printed thereon with an X-ray impervious ink is provided on the support portion via a first adhesive layer.

2. The mark-bearing support as claimed in claim 1, which is in the form of a rectangular parallelepiped.

3. The mark-bearing support as claimed in claim 1, wherein a second adhesive layer for temporarily holding the dental X-ray film pack thereon is provided over the X-ray pervious sheet and a release sheet is additionally provided over the second adhesive layer.

4. The mark-bearing support as claimed in claim 3, wherein the first mark is on an outer surface of the X-ray pervious sheet.

5. The mark-bearing support as claimed in claim 3, wherein the first mark is on an inner surface of the X-ray pervious sheet.

6. The mark-bearing support as claimed in claim 3, wherein an X-ray pervious second mark identical to the first mark is provided on a surface of the X-ray pervious bite portion, said surface being other than the support portion, in such a way that the second mark is easily externally visible.

7. The mark-bearing support as claimed in claim 1, wherein the X-ray impervious ink is a lead-containing ink.

8. The mark-bearing support as claimed in claim 1, wherein the first mark consists of at least one of numbers and alphabetical letters; and the first mark is in mirror image so that when X-rays are irradiated onto an X-ray film of the dental X-ray film pack through the bite portion, the first mark is imprinted in normal appearance on the X-ray film.

9. A mark-bearing support for a dental X-ray film pack, said mark-bearing support comprising:
    an X-ray pervious bite portion adapted to be clenched between upper and lower teeth; and
    a support portion means for temporarily holding the dental X-ray film pack thereon;
    wherein the support portion is provided with a first mark formed of an X-ray impervious material; and
    wherein the first mark is printed directly on the support portion with an X-ray impervious ink.

10. The mark-bearing support as claimed in claim 9, wherein the X-ray impervious ink is a lead-containing ink.

11. The mark-bearing support as claimed in claim 9, wherein the mark-bearing support is in the form of a rectangular parallelepiped.

12. The mark-bearing support as claimed in claim 9, wherein the first mark consists of at least one number or letter; and wherein the first mark is in mirror image so that when X-rays are irradiated onto an X-ray film of the dental X-ray film pack through the bite portion, the first mark is imprinted in normal appearance on the X-ray film.

13. A process for producing a plurality of mark-bearing supports adapted to hold dental X-ray film packs thereon, each of said supports having a bite portion adapted to be clenched between upper and lower teeth and a support portion means for temporarily holding the corresponding dental X-ray film pack thereon and being made of an X-ray pervious material, which comprises:
- printing a number of first marks at predetermined intervals with an X-ray impervious ink on an X-ray pervious base sheet;
- forming a first adhesive layer on one side of a block made of X-ray pervious material;
- applying the base sheet to the first adhesive layer;
- forming a second adhesive layer on an outer side of the applied base sheet;
- applying a release sheet to the second adhesive layer; and
- cutting the release sheet, base sheet and block between the individual first marks into smaller discrete blocks each having the bite portion and the support portion means.

14. The process as claimed in claim 13, wherein the base material is in the form of a rectangular parallelepiped; and before cutting the base material and base sheet, a like number of second marks identical to the first marks are applied with an X-ray pervious ink to an opposite side of the base material in such a way that the second marks are registered in position with the corresponding first marks printed with the X-ray impervious ink and the second marks are visible from the outside.

15. A process for producing a plurality of mark-bearing supports adapted to hold dental X-ray film packs thereon, each of said supports having a bite portion adapted to be clenched between upper and lower teeth and a support portion means for temporarily holding the corresponding dental X-ray film pack thereon and being made of an X-ray pervious material, which comprises:
- printing a number of marks at predetermined intervals with an X-ray impervious ink on one side of a block made of X-ray pervious material;
- forming an adhesive layer on said one side of the block;
- applying a release sheet to the adhesive layer; and
- cutting the release sheet and block between the individual marks into smaller discrete blocks each having the bite portion and the support portion means.

16. The process as claimed in claim 15, wherein the marks are printed in mirror image.

* * * * *